United States Patent [19]

McGee et al.

[11] Patent Number: 4,947,679

[45] Date of Patent: Aug. 14, 1990

[54] APPARATUS FOR DETERMINING RESIN GEL TIME

[75] Inventors: Robert L. McGee, Midland; David J. Nowak, Auburn; Gordon D. McCann; Frank L. Saunders, both of Midland, all of Mich.

[73] Assignee: The Dow Chemical Company, Midland, Mich.

[21] Appl. No.: 341,465

[22] Filed: Apr. 21, 1989

[51] Int. Cl.$^5$ .............................................. G01N 11/10
[52] U.S. Cl. ........................................ 73/64.1; 374/23
[58] Field of Search ................... 73/64.1, 59; 374/22, 374/23

[56] References Cited

U.S. PATENT DOCUMENTS

| | | | |
|---|---|---|---|
| 2,437,194 | 3/1948 | Harrington | 374/22 X |
| 3,077,106 | 2/1963 | Fink | 73/64.1 |
| 3,187,556 | 6/1965 | Ehlers | 374/22 |
| 3,587,295 | 6/1971 | Simons | 73/64.1 |
| 3,692,487 | 9/1972 | Sanz | 73/64.1 X |
| 3,704,099 | 11/1972 | Sanz | 73/59 X |
| 4,164,136 | 8/1979 | Wiggins et al. | 374/23 |
| 4,262,521 | 4/1981 | Beck | 73/64.1 X |
| 4,341,111 | 7/1982 | Husar | 73/64.1 |
| 4,622,846 | 11/1986 | Moon, Jr. et al. | 73/59 |
| 4,648,264 | 3/1987 | Freese et al. | 73/64.1 |

FOREIGN PATENT DOCUMENTS

| | | | |
|---|---|---|---|
| 1096083 | 12/1960 | Fed. Rep. of Germany | 73/64.1 |
| 88/05165 | 7/1988 | World Int. Prop. O. | 73/64.1 |

Primary Examiner—Hezron E. Williams
Assistant Examiner—Joseph W. Roskos

[57] ABSTRACT

The specification discloses a method and apparatus for determining the gel time of thermoset resins by using a disposable vial, a disposable spindle for insertion into the vial, a locking collar releasably secured to the disposable vial for mounting the vial in a permanent sample cup and holding it against rotation with respect thereto, and a spindle adaptor releasably receiving the disposable spindle for mounting same to the spindle mount of a conventional viscometer. The thermoset resin is located in the disposable vial along with the disposable spindle. The permanent sample cup including the disposable vial and its contents is located in a heater and the spindle adaptor is secured to the spindle mount of the viscometer. The viscometer is operated and the gel time is determined as the length of time it takes until the viscosity of the heated resin sample begins to increase sharply.

28 Claims, 3 Drawing Sheets

APPARATUS FOR DETERMINING RESIN GEL TIME

BACKGROUND OF THE INVENTION

The present invention relates to a method and apparatus for determining the gel time of thermoset resins at a particular reaction temperature. The gel time is the length of time it takes for the thermoset to begin to "gel" or harden.

One common prior art method for determining thermoset gel time involves placing the resin on a hot plate, stirring it until it becomes sticky and measuring the passage of time to that point. This is a rather imprecise method, but it is fairly popular because no expensive equipment is required to practice the method.

A much more precise method for measuring thermoset resin gel time involves the use of a very expensive piece of equipment known as a dynamic mechanical spectrometer (DMS) sold by Rheometrics. In accordance with this method, the thermoset resin is placed in a heated cup, and a plate or cone is lowered into the resin sample. The plate or cone is subjected to a vibratory spin, and the viscosity of the resin as measured by resistance to vibratory spin on an electric motor, is determined. The point at which the viscosity begins to rise quickly is the gel point, which establishes the gel time.

While this method and equipment yields accurate and reproducible results, the equipment is capital intensive. Further, the method must be finished before the thermoset cure is complete. The cup and the plate or cone must be cleaned before the cure is complete. Otherwise, the resin will have hardened in the cup and on the plate or cone, making it extremely difficult, and possibly impossible to clean.

SUMMARY OF THE INVENTION

In the present invention, the gel time for a thermoset resin is determined using a disposable spindle and a disposable vial. Adaptor means are provided for securing the spindle to a conventional viscometer and locking means are provided for locking the vial against rotation with respect to the conventional receiving chamber of a conventional viscometer. This apparatus can thus be used with relatively inexpensive, conventional viscometers, of the type sold for example by Brookfield. One does not need to worry about cleaning the spindle and sample container since the spindle and vial of the present invention are disposable. The thermoset resin can be allowed to cure completely in the test vial, with the disposable spindle in place.

These and other objects, advantages and features of the present invention will be more fully understood and appreciated by reference to the written specification and appended drawings.

DESCRIPTION OF THE PREFERRED EMBODIMENT

Figure 1:
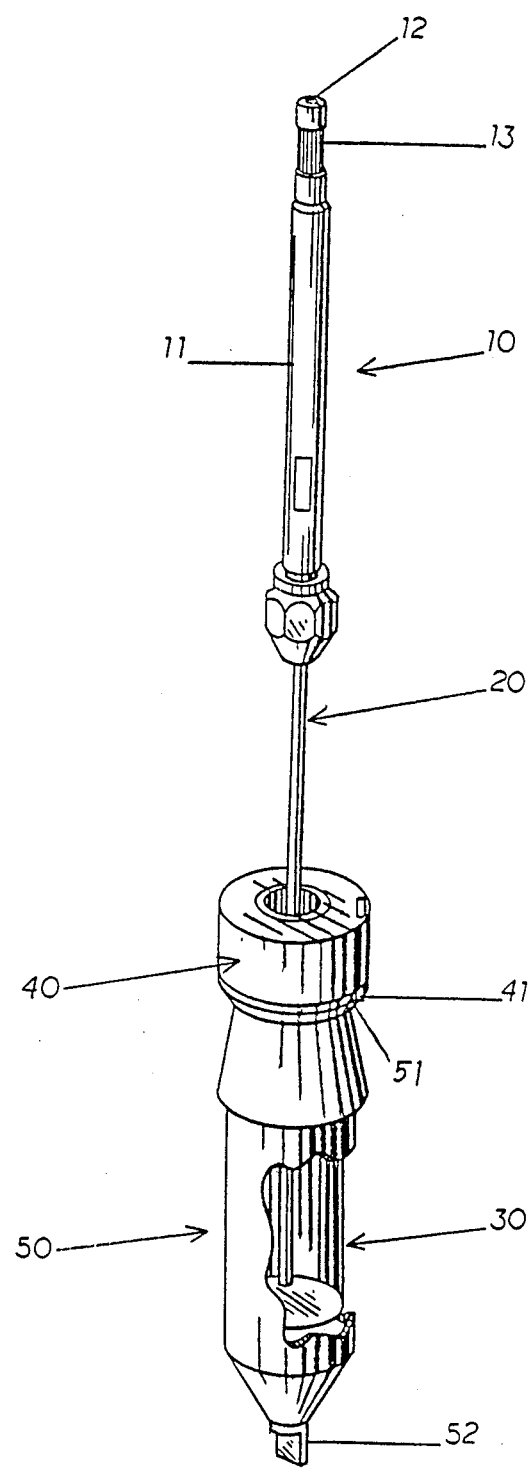
FIG. 1 is a perspective view of the apparatus of the present invention.
Figure 2:
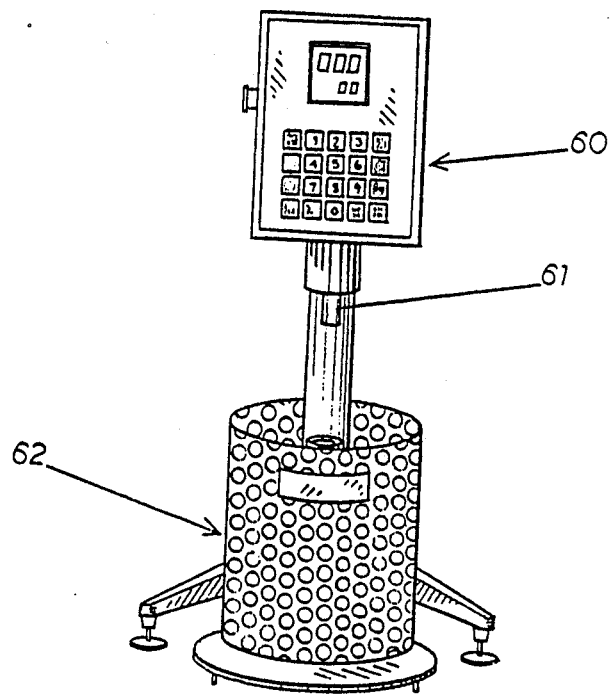
FIG. 2 is a perspective view of a conventional viscometer with which the apparatus of the present invention can be used.

In the preferred embodiment, a spindle adaptor 10 is provided for mounting disposable spindle 20 (FIG. 1) on the threaded spindle mounting shaft 61 of a conventional viscometer 60 (FIG. 2). In use, spindle 20 extends into a disposable vial 30 which fits snugly within the conventional sample container 50 of conventional viscometer 60 (FIG. 1). A locking collar 40 including a locking pin 41, which is received within a notch 51 at the top of permanent container 50, is threaded onto disposable container 30 for the purpose of locking disposable container 30 against rotation with respect to permanent sample container 50. Permanent sample container 50 fits down into the heating chamber 62 of viscometer 60, and is held against rotation with respect thereto by the small tab 52 projecting from the bottom thereof.

Figure 3:
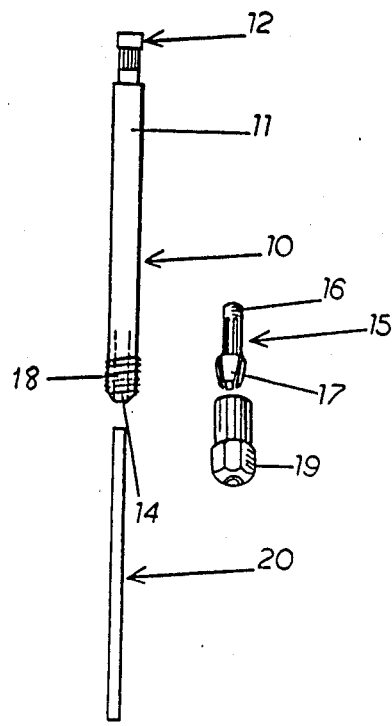
FIG. 3 is an exploded view of the disposable spindle and spindle adaptor of the present invention.

Spindle adaptor 10 comprises a shaft or body 11 having a left-hand threaded opening 12 at the upper end thereof (FIGS. 1 and 3). The outer surface of shaft 11 is knurled at 13, near the top of shaft 11, so that the user can grip shaft 11 when threading it onto the threaded spindle mount 61 of viscometer 60.

The opposite end of adaptor 11 also includes an opening 14 for receiving a collet 15. Collet 15 includes an upper cylindrical portion 16 which fits within opening 14 and a lower slightly enlarged, slotted cylindrical portion 17. The exterior surface of the lower end of shaft 11 is threaded at 18 for receiving a chuck or collet nut 19 thereon. Disposable spindle 20 fits up into and extends from collet 15 and chuck 19. By threading chuck 19 upwardly, one tightens the slotted lower end 17 or collet 15 down on the exterior surface of spindle 20 and holds it tightly in place.

Both spindle adaptor 11 and disposable spindle 20 are made of a material which is rigid and will not itself readily twist during operation of the apparatus. Steel is the preferred material for both. Spindle 20 must also be resistant to heat, since thermoset resin gel times are typically measured at temperatures of around 175° to 200° C.

Disposable spindle 20 should also have a relatively small diameter in order to measure the higher viscosities which will be encountered in a curing thermoset resin. A one-eighth inch diameter spindle is preferred, since that is equivalent to a number 7 Brookfield spindle. Thus a conventional Brookfield viscometer set to read viscosity as determined using a number 7 Brookfield spindle will accurately read the viscosities of the thermoset resin determined using the disposable one-eighth inch diameter spindle 20 of the present invention.

Figure 4:
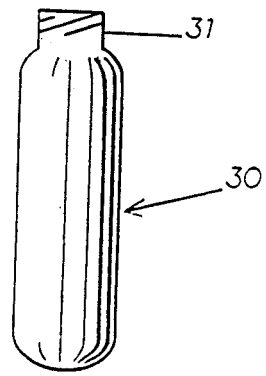
FIG. 4 is an elevational view of the disposable vial used in the present invention.

Disposable vial 30 must also be made of a heat resistant material. A glass vial having a threaded top 31 is preferred (FIG. 4). Vial 30 preferably fits snugly inside the permanent sample holder 50 of the conventional viscometer. This ensures good heat transfer from the conventional heater 62 through the walls of permanent container 50 and into disposable glass vial 30. A three dram vial having a 0.730 inch outside diameter fits snugly into the permanent sample container 50 of a Brookfield Model DV2 thermoviscometer apparatus.

Figure 5:
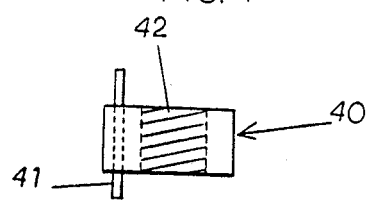
FIG. 5 is an elevational view of the locking collar used to lock the disposable vial against rotation with respect to a conventional viscometer.

Locking collar 40 includes internal threads 42 which thread onto the threads 31 of disposable vial 30 (FIG. 5). A locking pin 41 projects downwardly from collar 40 for fitting into a receiving notch 51 at the top of permanent container 50.

The stainless steel sample container 50 of the Brookfield Model DV2 viscometer includes a pair of notches 51 on either side of the top thereof. They are intended to facilitate insertion and removal of the permanent sample container 50 from the heater 62 of the apparatus. Locking pin 41 is configured so as to fit into either of these slots 51. Slots 51 are oriented at a slight angle to the vertical, not shown in the drawings. It is preferable to insert locking pin 41 into the slot 51 which slants downwardly in the direction of rotation of spindle 20 such that the tendency in operation is to turn pin 41 down into slot 51, rather than to ramp it up and out of slot 51.

In operation, a thermoset resin sample is placed in disposable glass vial 30. Preferably, about a five gram sample is used. There is about a minute to a minute and a half lag time until the sample comes up to the temperature of the heater. Consistency of sample size minimizes the impact of lag time on variability of result.

Locking collar 40 is threaded onto the threaded top 31 of vial 30. Disposable spindle 20 is inserted into spindle adaptor 10 and is locked in place using collet 15 and chuck 19 as described above. Disposable spindle 20 secured in adaptor 10 is then lowered into the resin sample located in disposable vial 30.

Vial 30 is then inserted into the permanent sample cup 50 of viscometer 60, with locking pin 41 of locking collar 40 engaging a receiving groove in permanent sample cup 50. Sample cup 50 is either already in or is then placed in heater 62 with bottom tab 52 preventing rotation of permanent sample cup 50. Spindle adaptor 10 is threaded onto the threaded spindle mounting shaft 61 of viscometer 60.

Figure 6:
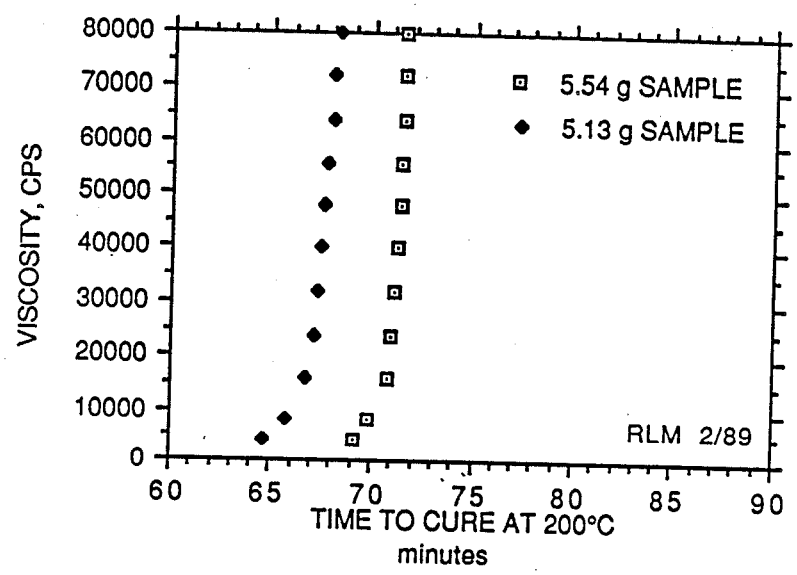
FIG. 6 is a typical viscosity profile obtained.

The sample is quickly brought to temperature in heater 62 while spindle 20 is rotated by the motor of viscometer 60. The viscosity as measured by viscometer 60 can be recorded on a suitable charting apparatus of the type typically available with such viscometers. The viscosity can also be read directly from the face of viscometer 60. The point at which viscosity begins to rise sharply is the gel point and the time it takes to reach that point is the gel time. A typical viscosity profile illustrating the sudden rise in viscosity after a length of time is shown in FIG. 6. The values obtained for both runs shown in FIG. 6 are within 10% which is a reasonable allowance for error.

While the preferred embodiment described above is especially adapted for use in conjunction with the Brookfield DV2 thermoviscometer apparatus, it will be appreciated by those skilled in the art that it could also be adapted for use with other types of viscometers. Modifications in the adaptor 10 and locking collar 40 may of course be required. Thus it will be understood that the above is merely a preferred embodiment of the invention and that various changes and alterations can be made without departing from the spirit and broader aspects thereof as set forth in the appended claims, which are to be interpreted in accordance with the principles of patent law, including the doctrine of equivalents.

The embodiments of the invention in which an exclusive property or privilege is claimed are defined as follows.

1. An apparatus for determining the gel time of thermoset resins comprising:
   a disposable vial made of a heat resistant, relatively inexpensive material such that said disposable vial can be discarded after a single test;
   a disposable spindle for insertion into said vial being made of a material which is resistant to torsional twisting, is heat resistant and is relatively inexpensive such that said spindle can be discarded after a single test;
   a locking collar releasably secured to said disposable vial for mounting said vial in a conventional viscometer heater and for locking said vial against rotation with respect thereto; and
   a spindle adaptor releasably receiving said disposable spindle and including means for securing said spindle adaptor to the spindle mount of a conventional viscometer.

2. The apparatus of claim 1 in which said disposable spindle comprises a steel rod.

3. The apparatus of claim 2 in which said disposable vial comprises a glass vial.

4. The apparatus of claim 3 in which said glass vial includes a threaded top; said locking collar including an internal thread and being threaded onto said glass top; said locking collar including detent means for engaging a heater to secure said collar and said disposable vial against rotation therein.

5. The apparatus of claim 4 in which said spindle adaptor includes a hollow end telescopically receiving said disposable spindle; said disposable spindle being received in a collet located in said hollow end of said adaptor; said adaptor including a threaded external end surface threadably receiving a chuck; said collet being tightened against said disposable spindle by threading said chuck upwardly over the threaded end of said adaptor.

6. The apparatus of claim 5 in which said adaptor includes a hollow upper end which is internally threaded for threading over the threaded spindle mount on a viscometer.

7. The apparatus of claim 6 in which said disposable spindle has a diameter of one-eighth of an inch.

8. The apparatus of claim 2 in which said disposable spindle has a diameter of one-eighth of an inch.

9. The apparatus of claim 1 in which said spindle adaptor includes a hollow end telescopically receiving said disposable spindle; said disposable spindle being received in a collet located in said hollow end of said adaptor; said adaptor including a threaded external end surface threadably receiving a chuck; said collet being tightened against said disposable spindle by threading said chuck upwardly over the threaded end of said adaptor.

10. The apparatus of claim 9 in which said adaptor includes a hollow upper end which is internally threaded for threading over the threaded spindle mount on a viscometer.

11. The apparatus of claim 1 in which said disposable vial comprises a glass vial.

12. The apparatus of claim 11 in which said glass vial includes a threaded top; said locking collar including an internal thread and being threaded onto said glass top; said locking collar including detent means for engaging a heater to secure said collar and said disposable vial against rotation therein.

13. An apparatus for determining the gel time of thermoset resins comprising:

a viscometer including a spindle mount;

a heater positioned below said spindle mount of said viscometer;

a permanent sample cup removably positioned in said heater and including detent means engaging said heater to prevent rotation of said permanent sample cup with respect to said heater;

a disposable vial made of a heat resistant, relatively inexpensive material such that said disposable vial can be discarded after a single test;

a disposable spindle for insertion into said vial, said disposable spindle being made of a material which is resistant to torsional twisting, is heat resistant and is relatively inexpensive such that such spindle can be discarded after a single test;

a locking collar releasably secured to said disposable vial;

said disposable vial being inserted into said permanent sample cup;

said locking collar and said permanent sample cup including mating detent and detent receiving means for holding said vial against rotation with respect to said permanent sample cup;

a spindle adaptor releasably receiving said disposable spindle and including means securing said spindle adaptor to said spindle mount of said viscometer.

14. The apparatus of claim 13 in which said disposable spindle comprises a steel rod.

15. The apparatus of claim 14 in which said disposable vial comprises a glass vial.

16. The apparatus of claim 15 in which said glass vial includes a threaded top; said locking collar including an internal thread and being threaded onto said glass top.

17. The apparatus of claim 16 in which said spindle adaptor includes a hollow end telescopically receiving said disposable spindle; said disposable spindle being received in a collet located in said hollow end of said adaptor; said adaptor including a threaded external end surface threadably receiving a chuck; said collet being tightened against said disposable spindle by threading said chuck upwardly over the threaded end of said adaptor.

18. The apparatus of claim 17 in which said spindle mount is threaded and said adaptor includes a hollow upper end which is internally threaded for threading over said threaded spindle mount.

19. The apparatus of claim 18 in which said disposable spindle has a diameter of one-eighth of an inch.

20. The apparatus of claim 14 in which said disposable spindle has a diameter of one-eighth of an inch.

21. The apparatus of claim 13 in which said spindle adaptor includes a hollow end telescopically receiving said disposable spindle; said disposable spindle being received in a collet located in said hollow end of said adaptor; said adaptor including a threaded external end surface threadably receiving a chuck; said collet being tightened against said disposable spindle by threading said chuck upwardly over the threaded end of said adaptor.

22. The apparatus of claim 21 in which said spindle mount is threaded and said adaptor includes a hollow upper end which is internally threaded for threading over said threaded spindle mount 23. The apparatus of claim 13 in which said disposable vial comprises a glass vial.

24. The apparatus of claim 23 in which said glass vial includes a threaded top; said locking collar including an internal thread and being threaded onto said glass top.

25. A method for determining the gel time of thermoset resins comprising:

positioning a disposable vial, made of a heat resistant, relatively inexpensive material such that said disposable vial can be discarded after a single test, within the permanent sample cup of a viscometer;

holding said permanent sample cup and said disposable vial against rotation with respect to one another;

securing a disposable spindle made of a material which is resistant to torsional twisting, is heat resistant and is relatively inexpensive such that said spindle can be discarded after a single test, to the spindle mount of a viscometer;

inserting said thermoset resin into said disposable vial;

inserting said disposable spindle into said disposable vial;

locating said permanent sample cup in a heater and securing said permanent sample cup against rotation with respect to said heater;

activating said viscometer and measuring the length of time until the viscosity of said thermoset resin begins to increase sharply.

26. The method of claim 25 in which a steel rod is used for said disposable spindle.

27. The method of claim 26 in which a glass vial is used for said disposable vial.

28. The method of claim 26 which includes using a disposable spindle with a diameter of one-eighth of an inch.

* * * * *